United States Patent [19]

Habeck et al.

[11] Patent Number: 6,090,374

[45] Date of Patent: Jul. 18, 2000

[54] COSMETIC AND PHARMACEUTICAL PREPARATIONS COMPRISING PHOTOSTABLE UV FILTERS

[75] Inventors: Thorsten Habeck, Meckenheim; Sylke Haremza, Neckargemünd; Volker Schehlmann, Römerberg; Horst Westenfelder, Neustadt; Thomas Wünsch, Speyer, all of Germany

[73] Assignee: BASF Aktiengesellschaft, Ludwigshagfen, Germany

[21] Appl. No.: 09/172,672

[22] Filed: Oct. 15, 1998

[30] Foreign Application Priority Data

Oct. 20, 1997 [DE] Germany ............... 197 46 001
Dec. 15, 1997 [DE] Germany ............... 197 55 650

[51] Int. Cl.⁷ .............. A61K 7/42; A61K 7/00; A61K 7/44
[52] U.S. Cl. .............. 424/59; 424/60; 424/400; 424/401
[58] Field of Search ............... 424/59, 60, 400, 424/401

[56] References Cited

U.S. PATENT DOCUMENTS

| | | |
|---|---|---|
| 3,275,520 | 9/1966 | Stobel . |
| 3,278,448 | 10/1966 | Lauerer . |
| 3,462,475 | 8/1969 | Strobel et al. . |
| 3,522,188 | 7/1970 | Strobel et al. . |
| 4,284,621 | 8/1981 | Preuss .................. 424/59 |
| 4,387,089 | 6/1983 | DePolo .................. 424/59 |
| 5,587,150 | 12/1996 | Deflandre ............... 424/59 |
| 5,830,441 | 11/1998 | Wang et al. ............. 424/59 |

FOREIGN PATENT DOCUMENTS

| | | |
|---|---|---|
| 251 398 | 1/1988 | European Pat. Off. . |
| 537742 | 4/1993 | European Pat. Off. . |
| 1368808 | 6/1964 | France . |
| 1087902 | 8/1960 | Germany . |
| 1246236 | 9/1971 | United Kingdom . |

OTHER PUBLICATIONS

*Chem. Abst.*, vol. 82, (1975), No. 25, AN 170573z.

*Primary Examiner*—Shelley A. Dodson
*Attorney, Agent, or Firm*—Keil & Weinkauf

[57] ABSTRACT

The use of substituted α-methylstyrene derivatives of the formula I,

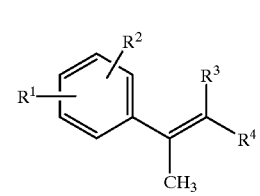

where the variables have the following meanings:

$R^1$ $C_4$–$C_{10}$-alkoxy, $C_1$–$C_{12}$-alkylamino, $C_1$–$C_{12}$-dialkylamino, substituents which confer solubility in water and which are selected from the group consisting of carboxylate, sulfonate or ammonium residues;

$R^2$ hydrogen, $C_2$–$C_{10}$-alkyl, $C_1$–$C_{12}$-alkoxy;

$R^3$ $COOR^5$, $COR^5$, $CONR^5R^6$, CN;

$R^4$ $COOR^5$, $COR^5$, $CONR^5R^6$, CN; where the substituents $R^3$ and $R^4$ are identical in each case;

$R^5$ and $R^6$ independently of one another hydrogen, $C_1$–$C_{12}$-alkyl, $C_2$–$C_{10}$-alkenyl, $C_3$–$C_{10}$-cycloalkyl, $C_3$–$C_{10}$-cycloalkenyl, aryl, hetaryl, unsubstituted or substituted;

as photostable UV filters in cosmetic and pharmaceutical preparations to protect the human skin or human hair from the sun's rays, alone or together with UV-absorbing compounds known per se for cosmetic and pharmaceutical preparations.

19 Claims, No Drawings

COSMETIC AND PHARMACEUTICAL PREPARATIONS COMPRISING PHOTOSTABLE UV FILTERS

The invention relates to the use of substituted α-methylstyrene derivatives as photostable UV filters in cosmetic and pharmaceutical preparations for protecting the human epidermis or human hair from UV radiation, specifically in the range from 320 to 400 nm.

The sunscreens employed in cosmetic and pharmaceutical preparations have the task of preventing or at least reducing the harmful effects of sunlight on human skin. However, these sunscreens also serve to protect other ingredients from decomposition or degradation by UV radiation. The intention in cosmetic formulations for hair is to reduce damage to keratin fibers by UV rays.

The sunlight reaching the surface of the earth contains UV-B (280 to 320 nm) and UV-A (>320 nm) radiation which is directly adjacent to the visible light region. The effect on human skin is manifested, especially in the case of UV-B radiation, by sunburn. Accordingly, the industry supplies a large number of substances which absorb UV-B radiation and thus prevent sunburn.

Dermatological investigations have now shown that UV-A radiation is also perfectly able to cause harm to skin and allergies by, for example, damaging keratin or elastin. This reduces the elasticity and water-storage capacity of the skin, ie. the skin becomes less supple and is prone to wrinkling. The noticeably high incidence of skin cancer in areas where the incident sunlight is strong shows that there is evidently also damage to the genetic information in the cells caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the desired effect with use of a minimum amount, these sunscreens ought additionally to have a high specific extinction. In addition, sunscreens for cosmetic products must also satisfy a large number of other requirements, for example good solubility in cosmetic oils, high stability of the emulsions produced with them, toxicological acceptability and little intrinsic odor and slight intrinsic color.

Another requirement which sunscreens must satisfy is adequate photostability. However, this is ensured to only an inadequate extent, if at all, with the UV-A-absorbing sunscreens available to date.

French Patent No. 2 440 933 describes 4-(1,1-dimethylethyl)-4'-methoxydibenzoylmethane as UV-A filter. It is proposed to combine this specific UV-A filter, which is sold by GIVAUDAN under the name "PARSOL 1789", with various UV-B filters in order to absorb all UV rays with a wavelength from 280 to 380 nm.

However, this UV-A filter does not have sufficient photochemical stability, on use alone or in combination with UV-B filters, to ensure lasting protection of the skin during lengthy sunbathing, which means that repeated applications are necessary at regular and short intervals if effective protection of the skin from all UV rays is desired.

EP-A-0 514 491 therefore discloses the stabilization of UV-A filters having inadequate photostability by adding 2-cyano-3,3-diphenylacrylic esters which themselves act as filters in the UV-B region.

It has also been proposed in EP-A-0 251 398 to combine UV-A- and UV-B-absorbing chromophores in one molecule by a linker. This has the disadvantage that a free combination of UV-A and UV-B filters in the cosmetic preparation is no longer possible, and that difficulties in chemically linking the chromophores allow only certain combinations.

German Patent No. 1 087 902 describes the use of condensates of hydroxy- and alkoxybenzaldehydes and carbon acids as UV filters in industrial applications, for example in plastics.

DE 2 816 819 describes 4-methoxybenzylidenecyanoacetic esters as UV-A filters in cosmetic applications, although the photostability of the compounds disclosed in this patent is inadequate. Another disadvantage is that synthesis of the UV absorbers described therein results in cis/trans mixtures which, if they are employed as such, form an inhomogeneous mixture with different absorption properties. Elaborate purification is necessary for use of the pure isomers.

It is an object of the present invention to propose sunscreens for cosmetic and pharmaceutical purposes which have a high extinction for absorption in the UV-A region, are photostable, have little intrinsic color, ie. a sharp band structure, and are soluble in oil or water depending on substituents.

We have found that this object is achieved by using substituted α-methylstyrene derivatives of the formula I

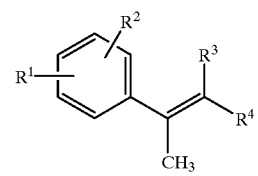

where the variables have the following meanings:
$R^1$ $C_4$–$C_{10}$-alkoxy, $C_1$–$C_{12}$-alkylamino, $C_1$–$C_{12}$-dialkylamino, substituents which confer solubility in water and which are selected from the group consisting of carboxylate, sulfonate or ammonium residues;
$R^2$ hydrogen, $C_2$–$C_{10}$-alkyl, $C_1$–$C_{12}$-alkoxy;
$R^3$ $COOR^5$, $COR^5$, $CONR^5R^6$, CN;
$R^4$ $COOR^5$, $COR^5$, $CONR^5R^6$, CN; where the substituents $R^3$ and $R^4$ are identical in each case;
$R^5$ and
$R^6$ independently of one another hydrogen, $C_1$–$C_{12}$-alkyl, $C_2$–$C_{10}$-alkenyl, $C_3$–$C_{10}$-cycloalkyl, $C_3$–$C_{10}$-cycloalkenyl, aryl, hetaryl, unsubstituted or substituted;
as photostable UV filters in cosmetic and pharmaceutical preparations to protect the human skin or human hair from the sun's rays, alone or together with UV-absorbing compounds known per se for cosmetic and pharmaceutical preparations.

Alkyl radicals which may be mentioned for $R^2$ are branched or unbranched $C_2$–$C_{10}$-alkyl chains, preferably ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl.

Alkyl radicals which may be mentioned for $R^5$ and $R^6$ are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

Alkenyl radicals $R^5$ and $R^6$ which may be mentioned are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals which may be mentioned for $R^5$ and $R^6$ are preferably branched or unbranched $C_3$–$C_{10}$-cycloalkyl radicals such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Cycloalkenyl radicals which may be mentioned for $R^5$ and $R^6$ are preferably branched or unbranched $C_3$–$C_{10}$-cycloalkenyl radicals having one or more double bonds, such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkenyl and cycloalkyl radicals may be substituted by one or more, eg. 1 to 3, radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms, such as sulfur, nitrogen whose free valencies can be saturated by hydrogen br $C_1$–$C_4$-alkyl, or oxygen, in the ring.

Suitable alkoxy radicals for $R^1$ are those having 4 to 10 carbon atoms, preferably having 4 to 8 carbon atoms.

Examples which may be mentioned are:

| | |
|---|---|
| 1-methylpropoxy- | n-butoxy- |
| n-pentoxy- | 2-methylpropoxy- |
| 3-methylbutoxy- | 1,1-dimethylpropoxy- |
| 2,2-dimethylpropoxy- | hexoxy- |
| 1-methyl-1-ethylpropoxy- | heptoxy- |
| octoxy- | 2-ethylhexoxy- |

Suitable alkoxy radicals for $R^2$ are those having 1 to 12 carbon atoms, preferably having 1 to 8 carbon atoms.

Examples which may be mentioned are:

| | |
|---|---|
| methoxy- | ethoxy- |
| isopropoxy | n-propoxy- |
| 1-methylpropoxy- | n-butoxy- |
| n-pentoxy- | 2-methylpropoxy- |
| 3-methylbutoxy- | 1,1-dimethylpropoxy- |
| 2,2-dimethylpropoxy- | hexoxy- |
| 1-methyl-1-ethylpropoxy- | heptoxy- |
| octoxy- | 2-ethylhexoxy- |

Suitable mono- or dialkylamino radicals for $R^1$ and $R^2$ are those containing alkyl radicals having 1 to 12 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl means aromatic rings or ring systems having 6 to 18 carbon atoms in the ring system, for example phenyl or naphthyl, each of which may be substituted by one or more radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Preference is given to unsubstituted or substituted phenyl, methoxyphenyl and naphthyl.

Hetaryl radicals are advantageously simple or fused aromatic ring systems having one or more heteroaromatic 3- to 7-membered rings. Heteroatoms which may be present are one or more nitrogen, sulfur and/or oxygen atoms in the ring or ring system.

Hydrophilic radicals, ie. ones allowing the compounds of the formula I to dissolve in water, for $R^1$ and $R^2$ are, for example, carboxyl and sulfo radicals and, in particular, their salts with any physiologically tolerated cations, such as the alkali metal salts or such as the trialkylammonium salts, such as tri-(hydroxyalkyl)ammonium salts or the 2-ammonio-2-methyl-1-propanol salts. Also suitable are ammonium radicals, in particular alkylammonium radicals, with any physiologically tolerated anions.

Preferred compounds of the formula I are those where
$R^1$ is $C_4$–$C_6$-alkoxy, in particular 3-methylbutoxy, n-butoxy and n-hexoxy, substituents which confer solubility in water and which are selected from the group consisting of carboxylate, sulfonate or ammonium residues;

$R^2$ is hydrogen, $C_2$–$C_4$-alkyl, ethyl, n-propyl, isopropyl, $C_1$–$C_8$-alkoxy, especially methoxy;

$R^3$ is CN $R^4$ is CN.

The substituents $R^1$ and $R^2$ can each be bonded in the ortho, meta or para position to the aromatic system. Particularly preferred compounds of the formula I are those where $R^1$ is in the para position and $R^2$ is in the meta position.

In addition, compounds of the formula I where the substituents $R^1$ to $R^4$ are present in the combination stated in Table 1 have particular photostable properties:

TABLE 1

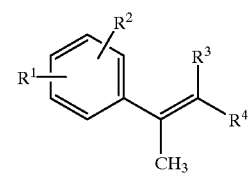

I

| $R^1$ | $R^2$ | $R^3$ | $R^4$ |
|---|---|---|---|
| n-Butoxy | H | CN | CN |
| n-Butoxy | Ethyl | CN | CN |
| n-Butoxy | n-Propyl | CN | CN |
| n-Butoxy | iso-Propyl | CN | CN |
| n-Butoxy | Methoxy | CN | CN |
| 3-Methylbutoxy | H | CN | CN |
| 3-Methylbutoxy | Ethyl | CN | CN |
| 3-Methylbutoxy | n-Propyl | CN | CN |
| 3-Methylbutoxy | iso-Propyl | CN | CN |
| 3-Methylbutoxy | Methoxy | CN | CN |
| n-Hexoxy | H | CN | CN |

TABLE 1-continued

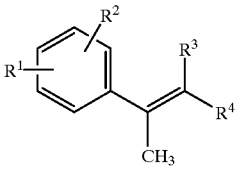

| R$^1$ | R$^2$ | R$^3$ | R$^4$ |
|---|---|---|---|
| n-Hexoxy | Ethyl | CN | CN |
| n-Hexoxy | n-Propyl | CN | CN |
| n-Hexoxy | iso-Propyl | CN | CN |
| n-Hexoxy | Methoxy | CN | CN |
| Ammonium | H | CN | CN |
| Ammonium | Ethyl | CN | CN |
| Ammonium | n-Propyl | CN | CN |
| Ammonium | iso-Propyl | CN | CN |
| Ammonium | Methoxy | CN | CN |
| Carboxylate | H | CN | CN |
| Carboxylate | Ethyl | CN | CN |
| Carboxylate | n-Propyl | CN | CN |
| Carboxylate | iso-Propyl | CN | CN |
| Carboxylate | Methoxy | CN | CN |
| Sulfonate | H | CN | CN |
| Sulfonate | Ethyl | CN | CN |
| Sulfonate | n-Propyl | CN | CN |
| Sulfonate | iso-Propyl | CN | CN |
| Sulfonate | Methoxy | CN | CN |

U.S. Pat. No. 3,275,520 has disclosed compounds of the formula II

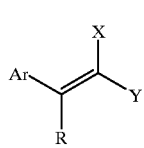

Concerning the profile of properties required for UV-A absorbers, such as, inter alia, good oil solubility, a UV stability >95%, and a high specific extinction, only the novel compounds of the formula I have been able to satisfy these conditions.

The novel α-methylstyrene derivatives of the formula I have the following advantages over the prior art:

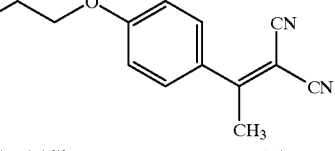

Oil solubility: >10%
$E_1^1$: 723
Photostability: >95%

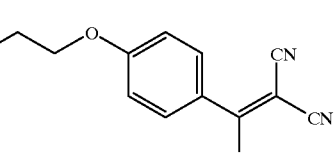

Oil solubility: >10%
$E_1^1$: 678
Photostability: >95%

Comparison compounds:

Oil solubility: >10%
$E_1^1$: 950
Photostability: 80%

Oil solubility: <2%
$E_1^1$: 800
Photostability: >95%

Oil solubility: <5%
$E_1^1$: 550
Photostability: >95%

Oil solubility: >10%
$E_1^1$: 400
Photostability: >95%

SUMMARY

[advantages over the prior art (U.S. Pat. No. 3,275,520)]:

α-Methyl in place of α-phenyl: better oil solubility, higher extinction
α-Methyl in place of α-hydrogen: better photostability
(R$^1$): OC$_4$H$_9$ in place of OCH$_3$: better oil solubility
(R$^1$): OC$_4$H$_9$ in place of OC$_{12}$H$_{25}$: higher extinction The compounds of the formula I to be used according to the invention can be prepared by condensation in accordance with the equation

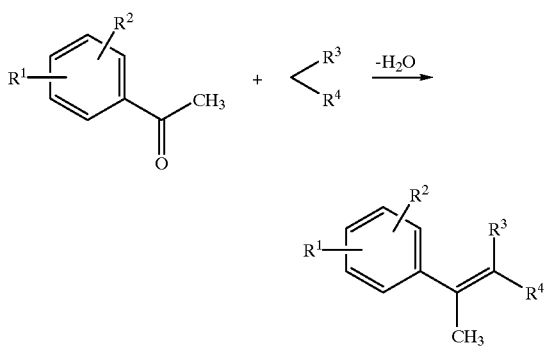

where $R^1$ to $R^4$ have the meanings stated in claim 1.

For example, reaction of 4-(3-methylbutoxy) acetophenone with malononitrile gives compound 1 in Tab. 2.

The present invention further relates to cosmetic and pharmaceutical preparations which comprise as sunscreens from 0.1 to 10% by weight, preferably 1 to 7% by weight, based on the total amount of cosmetic and pharmaceutical preparation, one or more of the compounds of the formula I, together with compounds which absorb in the UV-B region and are known for cosmetic and pharmaceutical preparations, employing the compounds of the formula I as a rule in a smaller amount than the UV-B-absorbing compounds.

Most of the sunscreens in the cosmetic and pharmaceutical preparations used for protecting the human epidermis consist of compounds which absorb UV light in the UV-B region, ie. in the region from 280 to 320 nm. The content of UV-A absorbers to be used according to the invention is, for example, from 10 to 90%, preferably 20 to 50%, based on the total amount of UV-B and UV-A absorbing substances.

The cosmetic and pharmaceutical preparations containing sunscreens are, as a rule, based on a carrier which comprises at least one oil phase. However, solely water-based preparations are also possible on use of compounds with hydrophilic substituents. Accordingly, oils, oil-in-water and water-in-oil emulsions, creams and pastes, protective lipstick compositions or nongreasy gels are suitable.

Sunscreen products of these types can accordingly be in liquid, pasty or solid form, for example as water-in-oil creams, oil-in-water creams and lotions, aerosol foam creams, gels, oils, grease sticks, dusting powders, sprays or hydroalcoholic lotions.

Examples of conventional cosmetic oil components are liquid paraffin, glyceryl stearate, isopropyl myristate, diisopropyl adipate, cetylstearyl 2-ethylhexanoate, hydrogenated polyisobutene, petrolatum, caprylic/capric acid triglycerides, microcrystalline wax, lanolin and stearic acid.

Examples of conventional cosmetic auxiliaries which may be suitable as additives are coemulsifiers, fats and waxes, stabilizers, thickeners, biogenic active substances, film formers, fragrances, dyes, pearlescent agents, preservatives, pigments, electrolytes (eg. magnesium sulfate) and pH regulators. Suitable and preferred coemulsifiers are known W/O and o/W emulsifiers such as polyglycerol esters, sorbitan esters or partially esterified glycerides. Typical examples of fats are glycerides; waxes which may be mentioned are, inter alia, beeswax, paraffin wax or microwaxes, where appropriate in combination with hydrophilic waxes. Stabilizers which can be employed are metal salts of fatty acids such as magnesium, aluminum and/or zinc stearate. Examples of suitable thickeners are crosslinked polyacrylic acids and their derivatives, polysaccharides, in particular xanthan gum, guar-guar, agar-agar, alginates and Tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active substances are plant extracts, protein hydrolysates and vitamin complexes. Examples of film formers which are in use are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlescent agents are glycol distearic esters such as ethylene glycol distearate, but also fatty acids and fatty acid monoglycol esters. Dyes which can be used are the substances suitable and approved for cosmetic purposes, as tabulated, for example, in the publication "Kosmetische Färbemittel" of the Farbstoffkommission der Deutschen Forschungsgemeinschaft, published in Verlag Chemie, Weinheim, 1984. These dyes are normally employed in a concentration of from 0.001 to 0.1% of the total weight of the mixture.

The total content of auxiliaries and additives can be from 1 to 80, preferably 6 to 40, % by weight, and the nonaqueous content ("active substance") can be from 20 to 80, preferably 30 to 70, % by weight, based on the compositions. The compositions can be produced in a manner known per se, ie. for example by hot, cold, hot—hot/cold or PIT emulsification. This is a purely mechanical process; no chemical reaction takes place.

Finally, it is also possible to use other substances which absorb in the UV-A region and are known per se as long as they are stable in the complete system of the combination of UV-B and UV-A filter to be used according to the invention.

Any UV filter substances are suitable for use in combination with the compounds of the formula I to be used according to the invention. Examples which may be mentioned are:

| No. | Substance | CAS No. (= acid) |
|---|---|---|
| 1 | 4-Aminobenzoic acid | 150-13-0 |
| 2 | 3-(4-Trimethylammonio)benzylidenebornan-2-one methyl sulfate | 52793-97-2 |
| 3 | 3,3,5-Trimethylcyclohexyl salicylate (Homosalate) | 118-56-9 |
| 4 | 2-Hydroxy-4-methoxybenzophenone (Oxybenzone) | 131-57-7 |

-continued

| No. | Substance | CAS No. (= acid) |
|---|---|---|
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methane-sulfonic acid) and its salts | 90457-82-2 |
| 7 | Polyethoxyethyl 4-bis(polyethoxy)amino-benzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (Sulisobenzone) and the sodium salt | 4065-45-6 |
| 13 | 3-(4-Methylbenzylidene)bornan-2-one | 36861-47-9 |
| 14 | 3-Benzylidenebornan-2-one | 15087-24-8 |
| 15 | 1-(4-Isopropylphenyl)-3-phenylpropane-1,3-dione | 63250-25-9 |
| 16 | 4-Isopropylbenzyl salicylate | 94134-93-7 |
| 17 | 2,4,6-Tri(o-2-ethylhexoxycarbonyl-anilino)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl o-aminobenzoate or: 5-Methyl-2-(1-methylethyl)cyclohexyl 2-aminobenzoate | 134-09-8 |
| 22 | Glyceryl p-aminobenzoate or: 4-Aminobenzoic acid 1-glyceryl ester | 136-44-7 |
| 23 | 2,2'-Dihydroxy-4-methoxybenzophenone (Dioxybenzone) | 131-53-3 |
| 24 | 2-Hydroxy-4-methoxy-4'-methylbenzophenone (Mexenone) | 1641-17-4 |
| 25 | Triethanolamine salicylate | 2174-16-5 |
| 26 | Dimethoxyphenylglyoxylic acid or: Sodium 3,4-dimethoxyphenylglyoxylate | 4732-70-1 |
| 27 | 3-(4-Sulfobenzylidene)bornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

Finally, mention may also be made of micronized pigments such as titanium dioxide and zinc oxide.

To protect human hair from UV rays, the sunscreens of the formula I according to the invention can be incorporated into shampoos, lotions, gels, hair sprays, aerosol foam creams or emulsions in concentrations of from 0.1 to 10% by weight, preferably 1 to 7% by weight. The particular formulations can be used inter alia for washing, coloring and setting the hair.

The compounds to be used according to the invention as a rule have a particularly high absorbance in the region of UV-A radiation with a sharp band structure. They are in addition readily soluble in cosmetic oils and can easily be incorporated into cosmetic formulations. Emulsions prepared using the compounds I show particularly high stability, the compounds I themselves show high photostability, and the preparations produced with I have a pleasant skin feel.

The UV filter action of the compounds of the formula I according to the invention can also be utilized for stabilizing active substances and auxiliaries in cosmetic and pharmaceutial formulations.

The invention also relates to compounds of the formula I for use as medicine and to pharmaceutical compositions for the preventive treatment of inflammations and allergies of the skin, and for preventing certain types of skin cancer, which comprise an effective amount of at least one compound of the formula I as active substance.

The pharmaceutical compositions according to the invention can be administered orally or topically. For oral administration, the pharmaceutical composition is in the form of, inter alia, pastilles, gelatin capsules, coated tablets, syrup, solution, emulsion or suspension. The pharmaceutical compositions are used topically for example as ointment, cream, gel, spray, solution or lotion.

EXAMPLES

I. Preparation

Example 1

Method for preparing compound No. 1 in Table 2

0.1 mol of 4-(3-methylbutoxy)acetophenone and 0.1 mol of malononitrile were dissolved in 100 ml of toluene and heated to reflux, and 20 ml of a mixture of ammonium acetate and glacial acetic acid were added dropwise. The water formed in the reaction was removed azeotropically. After cooling and washing with water, the organic phase was dried with sodium sulfate and concentrated under reduced pressure. The residue was crystallized from methanol/water.

Yield: 7.9 g (33% of theory). Purity: >99% (GC).

Compounds 2 to 4 in Table 2 were prepared in a similar way to Example 1.

TABLE 2

Table of synthesized compounds

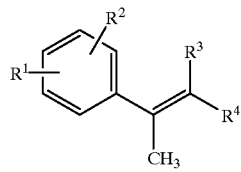

| Number | | λ max (nm) | $E_1^1$ |
|---|---|---|---|
| 1 | 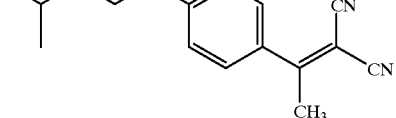 | 338 | 723 |
| 2 | 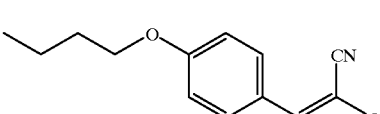 | 338 | 678 |
| 3 | 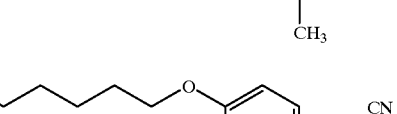 | 338 | 690 |
| 4 | 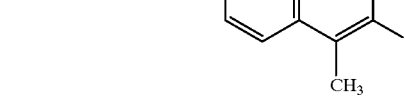 | 354 | 485 |

Example 2

Standardized method for determining the photostability (Suntest)

A 5% by weight alcoholic solution of the sunscreen to be tested is applied, using an Eppendorf pipette (20 ml), to the milled area on a glass plate. Owing to the presence of alcohol, the solution is distributed uniformly on the roughened glass surface. The amount applied corresponds to the amount of sunscreen required to obtain an average sun protection factor in suncreams. In the test, 4 glass plates are irradiated each time. The evaporation time and the irradiation each last for 30 minutes. The glass plates are cooled slightly during the irradiation by a water cooling system located at the base of the Suntest apparatus. The temperature inside the Suntest apparatus during the irradiation is 40° C. After the samples have been irradiated, they are washed with ethanol into a dark 50 ml graduated flask and measured in a photometer. The blank samples are applied in the same way to glass plates and evaporated at room temperature for 30 minutes. Like the other samples, they are washed off with ethanol and diluted to 100 ml and measured.

Comparative—Photostability:

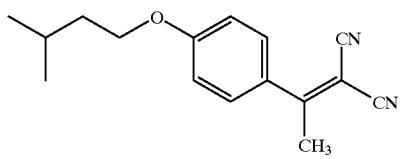
Photostability: >95%

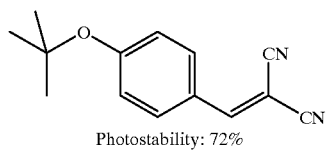
Photostability: 72%

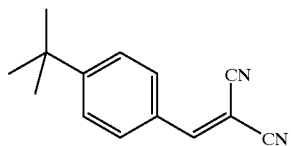
Photostability: 81%

-continued

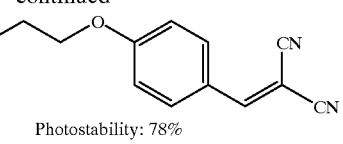
Photostability: 78%

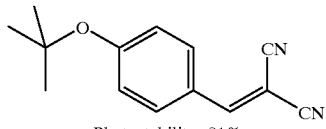
Photostability: 81%

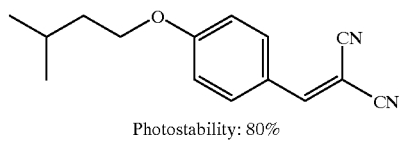
Photostability: 80%

General method for preparing emulsions for cosmetic purposes

All the oil-soluble ingredients are heated to 85° C. in a stirred vessel. When all the ingredients have melted or are present as liquid phase, the aqueous phase is incorporated by homogenization. The emulsion is cooled to about 40° C. with stirring, is perfumed and homogenized, and is then cooled to 25° C. while stirring continuously.

Preparations

Example 3
Lip care composition
Content
% by weight

| | |
|---|---|
| ad 100 | Eucerinum anhydricum |
| 10.00 | Glycerol |
| 10.00 | Titanium dioxide |
| 5.00 | Compound No. 1 in Table 2 |
| 8.00 | Octyl methoxycinnamate |
| 5.00 | Zinc oxide |
| 4.00 | Castor oil |
| 4.00 | Pentaerythrityl stearate/caprate/caprylate/adipate |
| 3.00 | Glyceryl stearate SE |
| 2.00 | Beeswax |
| 2.00 | Microcrystalline wax |
| 2.00 | Quaternium-18 bentonite |
| 1.50 | PEG-45/Dodecyl glycol copolymer |

Example 4
Lip care composition
Content
% by weight

| | |
|---|---|
| ad 100 | Eucerinum anhydricum |
| 10.00 | Glycerol |
| 10.00 | Titanium dioxide |
| 5.00 | Compound No. 2 in Table 2 |
| 8.00 | Octyl methoxycinnamate |
| 5.00 | Zinc oxide |
| 4.00 | Castor oil |
| 4.00 | Pentaerythrityl stearate/caprate/caprylate/adipate |
| 3.00 | Glyceryl stearate SE |
| 2.00 | Beeswax |
| 2.00 | Microcrystalline wax |
| 2.00 | Quaternium-18 bentonite |
| 1.50 | PG-45/dodecyl glycol copolymer |

Example 5
Sunblocker composition with micropigments
Content
% by weight

| | |
|---|---|
| ad 100 | Water |
| 10.00 | Octyl methoxycinnamate |
| 6.00 | PEG-7-hydrogenated castor oil |
| 6.00 | Titanium dioxide |
| 5.00 | Compound No. 1 in Table 2 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Dimethicone |
| 0.50 | PEG-40-hydrogenated castor oil |
| 0.50 | Tocopheryl acetate |
| 0.50 | Phenoxyethanol |
| 0.20 | EDTA |

Example 6
Sunblocker composition with micropigments
Content
% by weight

| | |
|---|---|
| ad 100 | Water |
| 10.00 | Octyl methoxycinnamate |
| 6.00 | PEG-7-hydrogenated castor oil |
| 6.00 | Titanium dioxide |
| 5.00 | Compound No. 2 in Table 2 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Dimethicone |
| 0.50 | PEG-40-hydrogenated castor oil |
| 0.50 | Tocopheryl acetate |
| 0.50 | Phenoxyethanol |
| 0.20 | EDTA |

Example 7
Nongreasy gel
Content
% by weight

| | |
|---|---|
| ad 100 | Water |
| 8.00 | Octyl methoxycinnamate |
| 7.00 | Titanium dioxide |
| 5.00 | Compound No. 1 in Table 2 |
| 5.00 | Glycerol |
| 5.00 | PEG-25 PABA |
| 1.00 | 4-Methylbenzylidenecamphor |
| 0.40 | Acrylate C10–C30 alkyl acrylate crosspolymer |
| 0.30 | Imidazolidinylurea |
| 0.25 | Hydroxyethylcellulose |

-continued

| | |
|---|---|
| 0.25 | Sodium methylparaben |
| 0.20 | Disodium EDTA |
| 0.15 | Fragrance |
| 0.15 | Sodium propylparaben |
| 0.10 | Sodium hydroxide |

Example 8
Nongreasy gel
Content
% by weight

| | |
|---|---|
| ad 100 | Water |
| 8.00 | Octyl methoxycinnamate |
| 7.00 | Titanium dioxide |
| 5.00 | Compound No. 2 in Table 2 |
| 5.00 | Glycerol |
| 5.00 | PEG-25 PABA |
| 1.00 | 4-Methylbenzylidenecamphor |
| 0.40 | Acrylate C10–C30 alkyl acrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

Example 9
Suncream (SPF 20)
Content
% by weight

| | |
|---|---|
| ad 100 | Water |
| 8.00 | Octyl methoxycinnamate |
| 8.00 | Titanium dioxide |
| 6.00 | PEG-7-hydrogenated castor oil |
| 5.00 | Compound No. 1 in Table 2 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |
| 0.20 | Disodium EDTA |
| 0.15 | Propylparaben |

Example 10
Suncream (SPF 20)
Content
% by weight

| | |
|---|---|
| ad 100 | Water |
| 8.00 | Octyl methoxycinnamate |
| 8.00 | Titanium dioxide |
| 6.00 | PEG-7-hydrogenated castor oil |
| 5.00 | Compound No. 2 in Table 2 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |
| 0.20 | Disodium EDTA |
| 0.15 | Propylparaben |

Example 11
Water-resistant suncream
Content
% by weight

| | |
|---|---|
| ad 100 | Water |
| 8.00 | Octyl methoxycinnamate |
| 5.00 | PEG-7-hydrogenated castor oil |
| 5.00 | Propylene glycol |
| 4.00 | Isopropyl palmitate |
| 4.00 | Caprylic/capric triglyceride |
| 5.00 | Compound No. 1 in Table 2 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

Example 12
Water-resistant suncream
Content
% by weight

| | |
|---|---|
| ad 100 | Water |
| 8.00 | Octyl methoxycinnamate |
| 5.00 | PEG-7-hydrogenated castor oil |
| 5.00 | Propylene glycol |
| 4.00 | Isopropyl palmitate |
| 4.00 | Caprylic/capric triglyceride |
| 5.00 | Compound No. 2 in Table 2 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

Example 13
Sun milk (SPF 6)
Content
% by weight

| | |
|---|---|
| ad 100 | Water |
| 10.00 | Mineral oil |

-continued

| | |
|---|---|
| 6.00 | PEG-7-hydrogenated castor oil |
| 5.00 | Isopropyl palmitate |
| 3.50 | Octyl methoxycinnamate |
| 5.00 | Compound No. 1 in Table 2 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

Example 14

Sun Milk (SPF 6)
Content
% by weight

| | |
|---|---|
| ad 100 | Water |
| 10.00 | Mineral oil |
| 6.00 | PEG-7-hydrogenated castor oil |
| 5.00 | Isopropyl palmitate |
| 3.50 | Octyl methoxycinnamate |
| 5.00 | Compound No. 2 in Table 2 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

What is claimed is:

1. A method for protecting human skin or hair from UV radiation which comprises treating the skin or the hair with an effective amount of an α-methylstyrene of the formula I,

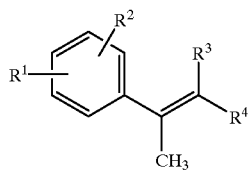

wherein
$R^1$ is $C_1$–$C_{10}$-alkoxy, $C_1$–$C_{12}$-alkylamino, $C_1$–$C_{12}$-dialkylamino or a substituent selected from the group consisting of carboxylate, sulfonate and ammonium residues;
$R^2$ is hydrogen, $C_2$–$C_{10}$-alkyl, $C_1$–$C_{12}$-alkoxy;
$R^3$ and
$R^4$ are identical and are $COOR^5$, $COR^5$, $CONR^5R^6$ or CN;
$R^5$ and $R^6$ are independently of one another hydrogen, $C_1$–$C_{12}$-alkyl, $C_2$–$C_{10}$-alkenyl, $C_3$–$C_{10}$-cycloalkyl, $C_3$–$C_{10}$-cycloalkenyl, aryl, hetaryl, unsubstituted or substituted;
alone or in combination with one or more UV-absorbing compounds known per se for cosmetic and pharmaceutical preparations.

2. The method of claim 1 for protecting the skin or the hair from UV-A radiation.

3. The method of claim 1, wherein the skin or the hair is treated with a cosmetic or pharmaceutical preparation comprising the α-methylstyrene of the formula I.

4. The method of claim 1, wherein
$R^1$ is $C_4$–$C_6$-alkoxy or a substituent selected from the group consisting of carboxylate, sulfonate and ammonium residues;
$R^2$ is hydrogen, $C_2$–$C_4$-alkyl or $C_1$–$C_4$-alkoxy;
$R^3$ and
$R^4$ are CN.

5. A cosmetic or pharmaceutical preparation comprising sunscreens to protect the human epidermis or human hair from UV light in the range of from 280 to 400 nm, which comprises a cosmetically or pharmaceutically suitable carrier and an effective amount of one or more compounds of the formula I defined in claim 1 and optionally one or more UV-absorbing compounds known per se for cosmetic and pharmaceutical preparations.

6. The preparation defined in claim 5, wherein
$R^1$ is $C_4$–$C_6$-alkoxy or a substituent selected from the group consisting of carboxylate, sulfonate and ammonium residues;
$R^2$ is hydrogen, $C_2$–$C_4$-alkyl or $C_1$–$C_4$-alkoxy;
$R^3$ and
$R^4$ are CN.

7. A pharmaceutical preparation comprising an effective amount of at least one compound of the formula I as set forth in claim 1.

8. The preparation defined in claim 5, wherein $R^1$ denotes 3-methylbutoxy, n-butoxy, n-hexoxy or a substituent selected from the group consisting of carboxylate, sulfonate and ammonium residues.

9. The preparation defined in claim 5, wherein $R^2$ denotes hydrogen, ethyl, n-propyl, isopropyl or methoxy.

10. The preparation defined in claim 5, wherein $R^3$ and $R^4$ are CN.

11. The preparation defined in claim 5, wherein $R^1$ is bonded in para position of the phenyl ring.

12. The preparation defined in claim 5, wherein $R^2$ is bonded in meta position of the phenyl ring.

13. The preparation defined in claim 5, wherein $R^1$ is bonded in para position and $R^2$ is bonded in meta position of the phenyl ring.

14. The method of claim 1, wherein $R^1$ denotes 3-methylbutoxy, n-butoxy, n-hexoxy or a substituent selected from the group consisting of carboxylate, sulfonate and ammonium residues.

15. The method of claim 1, wherein $R^2$ denotes hydrogen, ethyl, n-propyl, isopropyl or methoxy.

16. The method of claim 1, wherein $R^3$ and $R^4$ are CN.

17. The method of claim 1, wherein $R^1$ is bonded in para position of the phenyl ring.

18. The method of claim 1, wherein $R^2$ is bonded in meta position of the phenyl ring.

19. The method of claim 1, wherein $R^1$ is bonded in para position and $R^2$ is bonded in meta position of the phenyl ring.

* * * * *